United States Patent
Ni

(10) Patent No.: US 8,983,572 B2
(45) Date of Patent: Mar. 17, 2015

(54) SYSTEM AND METHOD FOR PATIENT SELECTION IN TREATING SLEEP DISORDERED BREATHING

(75) Inventor: Quan Ni, Shoreview, MN (US)

(73) Assignee: Inspire Medical Systems, Inc., Maple Grove, MN (US)

( * ) Notice: Subject to any disclaimer, the term of this patent is extended or adjusted under 35 U.S.C. 154(b) by 466 days.

(21) Appl. No.: 13/283,928

(22) Filed: Oct. 28, 2011

(65) Prior Publication Data

US 2012/0108945 A1    May 3, 2012

Related U.S. Application Data

(60) Provisional application No. 61/408,344, filed on Oct. 29, 2010.

(51) Int. Cl.
| | | |
|---|---|---|
| A61B 5/00 | (2006.01) | |
| A61B 5/087 | (2006.01) | |
| A61B 6/03 | (2006.01) | |
| A61B 6/00 | (2006.01) | |
| A61B 8/08 | (2006.01) | |

(52) U.S. Cl.
CPC ............ *A61B 5/0878* (2013.01); *A61B 5/6852* (2013.01); *A61B 6/032* (2013.01); *A61B 6/487* (2013.01); *A61B 6/50* (2013.01); *A61B 8/08* (2013.01); *A61B 2562/043* (2013.01)
USPC ............................ 600/410; 600/411; 600/425

(58) Field of Classification Search
CPC .......... A61B 6/032; A61B 6/50; A61B 6/487; A61B 8/00
USPC .......................................... 600/410, 411, 425
See application file for complete search history.

(56) References Cited

U.S. PATENT DOCUMENTS

| | | | |
|---|---|---|---|
| 5,158,080 A | 10/1992 | Kallok | |
| 5,245,995 A | 9/1993 | Sullivan et al. | |
| 5,344,438 A | 9/1994 | Testerman | |
| 5,860,938 A | 1/1999 | LaFontaine | |
| 7,186,220 B2 | 3/2007 | Stahmann et al. | |

(Continued)

FOREIGN PATENT DOCUMENTS

| | | |
|---|---|---|
| WO | 2008048471 | 4/2008 |
| WO | 2009048580 | 4/2009 |

(Continued)

OTHER PUBLICATIONS

Alan R. Schwartz, MD, et al., Therapeutic Electrical Stimulation of the Hypoglossal Nerve in Obstructive Sleep Apnea, Arch Otolaryngol Head Neck Surg/vol. 127, Oct. 2001, 8 pages.

(Continued)

*Primary Examiner* — Rajeev Siripurapu
(74) *Attorney, Agent, or Firm* — Dicke, Billig & Czaja, PLLC

(57) ABSTRACT

A system and method provides for determining patient eligibility for receiving an implantable upper airway stimulation system. Images and sensed data are obtained regarding an upper airway of a patient. Based on the obtained image and sensed data, an obstruction vector is determined according to a location, a pattern, and a degree of obstruction along the upper airway. A patient candidate filter is applied against a patient health profile. Patient eligibility is determined based on the obstruction vector and application of the patient candidate filter.

21 Claims, 6 Drawing Sheets

(56) References Cited

U.S. PATENT DOCUMENTS

| | | | |
|---|---|---|---|
| 7,189,204 | B2 | 3/2007 | Ni et al. |
| 7,252,640 | B2 | 8/2007 | Ni et al. |
| 7,396,333 | B2 | 7/2008 | Stahmann et al. |
| 7,468,040 | B2 | 12/2008 | Hartley et al. |
| 7,469,697 | B2 | 12/2008 | Lee et al. |
| 7,510,531 | B2 | 3/2009 | Lee et al. |
| 7,572,225 | B2 | 8/2009 | Stahmann et al. |
| 7,603,170 | B2 | 10/2009 | Hatlestad |
| 7,610,094 | B2 | 10/2009 | Stahmann et al. |
| 7,644,714 | B2 | 1/2010 | Atkinson et al. |
| 7,697,968 | B2 | 4/2010 | Moore |
| 7,725,195 | B2 | 5/2010 | Lima et al. |
| 7,809,442 | B2 | 10/2010 | Bolea et al. |
| 2004/0162499 | A1 | 8/2004 | Nagai et al. |
| 2005/0042589 | A1 | 2/2005 | Hatlestad et al. |
| 2005/0043772 | A1 | 2/2005 | Stahmann et al. |
| 2005/0076908 | A1 | 4/2005 | Lee et al. |
| 2005/0080348 | A1 | 4/2005 | Stahmann et al. |
| 2005/0080461 | A1 | 4/2005 | Stahmann et al. |
| 2005/0081847 | A1 | 4/2005 | Lee et al. |
| 2005/0085865 | A1 | 4/2005 | Tehrani |
| 2005/0085866 | A1 | 4/2005 | Tehrani |
| 2005/0085868 | A1 | 4/2005 | Tehrani |
| 2005/0085869 | A1 | 4/2005 | Tehrani |
| 2005/0101833 | A1 | 5/2005 | Hsu |
| 2005/0113710 | A1 | 5/2005 | Stahmann et al. |
| 2005/0115561 | A1 | 6/2005 | Stahmann et al. |
| 2005/0165457 | A1 | 7/2005 | Benser |
| 2005/0209513 | A1 | 9/2005 | Heruth |
| 2005/0209643 | A1 | 9/2005 | Heruth |
| 2006/0079802 | A1 | 4/2006 | Jensen |
| 2006/0142815 | A1 | 6/2006 | Tehrani |
| 2006/0241708 | A1 | 10/2006 | Boute |
| 2006/0266369 | A1 | 11/2006 | Atkinson et al. |
| 2007/0233204 | A1 | 10/2007 | Lima et al. |
| 2008/0103545 | A1 | 5/2008 | Bolea et al. |
| 2008/0132802 | A1 | 6/2008 | Ni et al. |
| 2008/0294060 | A1 | 11/2008 | Haroal et al. |
| 2009/0024047 | A1 | 1/2009 | Shipley et al. |
| 2009/0062882 | A1 | 3/2009 | Zhang et al. |
| 2009/0112116 | A1 | 4/2009 | Lee et al. |
| 2010/0094379 | A1 | 4/2010 | Meadows et al. |
| 2010/0174341 | A1 | 7/2010 | Bolea et al. |
| 2010/0198103 | A1 | 8/2010 | Meadows et al. |
| 2010/0241195 | A1 | 9/2010 | Meadows et al. |
| 2011/0093036 | A1 | 4/2011 | Mashiach |
| 2011/0112601 | A1 | 5/2011 | Meadows et al. |
| 2011/0152965 | A1 | 6/2011 | Mashiach et al. |
| 2012/0022365 | A1* | 1/2012 | Mansfield ............... 600/425 |

FOREIGN PATENT DOCUMENTS

| | | |
|---|---|---|
| WO | 2009048581 | 4/2009 |
| WO | 2009135138 | 11/2009 |
| WO | 2009135140 | 11/2009 |
| WO | 2009135142 | 11/2009 |
| WO | 2009140636 | 11/2009 |
| WO | 2010039853 | 4/2010 |
| WO | 2010057286 | 5/2010 |
| WO | 2010059839 | 5/2010 |
| WO | 2010117810 | 10/2010 |
| WO | 2011112843 | 9/2011 |

OTHER PUBLICATIONS

Magne Tvinnereim et al., Pressure Recordings—A Method for Detecting Site of Upper Airway Obstruction in Obstructive Sleep Apnea Syndrome, Acta Otolaryngol (Stockh) 1992; Suppl. 492: 132-140, 7 pages.

Olav Skatvedt, Localization of Site of Obstruction in Snorers and Patients with Obstructive Sleep Apnea Syndrome: A Comparison of Fiberoptic Nasopharyngoscopy and Pressure Measurements, Acta Otolaryngol (Stockh) 1993: 113: 206-209, 5 pages.

Eric J. Kezirian et al., Electrical Stimulation of the Hypoglossal Nerve in the Treatment of Obstructive Sleep Apnea, Sleep Medical Reviews (2009), doi: 10.1016/j.smrv.2009.10.009, 7 pages.

Eric J. Kezirian, Drug-induced Sleep Endoscopy, Operative Techniques in Otolaryngology (2006) 17, 230-232, 3 pages.

M. Carrasco Llatas et al., Our Findings in the Sleep Endoscopy Exams, Acta Otorrinolaringol Esp 2005; 56: 17-21, 5 pages.

M.B. Pringle & C.B. Croft, A Grading System for Patients with Obstructive Sleep Apnoea—Based on Sleep Nasendoscopy, Clin. Otolaryngol. 1993, 18, 480-484, 5 pages.

Bhik T. Kotecha et al., Sleep Nasendoscopy: A 10-Year Retrospective Audit Study, Eur Arch Otorhinolaryngol (2007) 264: 1361-1367, DOI 10.1007/s00405-007-0366-1, 7 pages.

Ama Johal et al., Sleep Nasendoscopy: A Diagnostic Tool for Predicting Treatment Success with Mandibular Advancement Splints in Obstructive Sleep Apnoea, European Journal of Orthodontics 27 (2005) 607-614, doi: 10.1093/ejo/cji063, Advance Access Publication Jul. 27, 2005, 8 pages.

Graham Roblin et al., Target-Controlled Infusion in Sleep Endoscopy, The Laryngoscope, Lippincott Williams & Wilkins, Inc., Philadelphia, 2001 The American Laryngological, Rhinological and Octological Society, Inc., Laryngoscope 111: Jan. 2001, 2 pages.

S. Berry et al., Validity of Sleep Nasendoscopy in the Investigation of Sleep Related Breathing Disorders, The Laryngoscope, Lippincott Williams & Wilkins, Inc., Copyright 2005, The American Laryngological, Rhinological and Octological Society, Inc., Laryngoscope 115: Mar. 2005, 3 pages.

Gideon Bachar et al., Laryngeal and Hypopharyngeal Obstruction in Sleep Disordered Breathing Patients, Evaluated by Sleep Endoscopy, Eur Arch Otorhinolaryngol (2008) 265:1397-1402, DOI 10.1007/s00405-008-0637-5, 6 pages.

David W. Hudgel, Variable Site of Airway Narrowing Among Obstructive sleep Apnea Patients, 0161-7567/86, Copyright 1986 the American Psychological Society, 7 pages.

David W. Hudgel, Properties of Upper Airway During Sleep, Ear, Nose, Throat J. Jan. 1993; 72(1): 42-5, 6 pages.

Avram R. Gold et al., The Pharyngeal Critical Pressure, The Whys and Hows of Using Nasal Continuous Positive Airway Pressure Diagnostically, Chest 1996; 110:1077-88, CHEST/110/4/ Oct. 1996, 14 pages.

Tucker Woodson et al., A Multisensor Solid-state Pressure Manometer to Identify the Level of Collapse in Obstructive Sleep Apnea, Otolaryngology—Head and Neck Surgery, vol. 107 No. 5, Nov. 1992, 23/1/41101, pp. 651-656, 6 pages.

A. Dundar et al., Patient Selection and Surgical Results in Obstructive Sleep Apnea, Eur Arch Otorhinolaryngol (1997) 254 (Suppl. 1): S157-S161, copyright Springer-Verlag 1997, 5 pages.

Han Demin, MD et al., Determining the Site of Airway Obstruction in Obstructive Sleep Apnea with Airway Pressure Measurements During Sleep, The Laryngoscope, Lippincott Williams & Wilkins, Inc., Philadelphia, copyright 2002, The American Laryngological, Rhinological and Octological Society, Inc., Larygoscope 112: Nov. 2002, 5 pages.

Richard J. Schwab et al., Identification of Upper Airway Anatomic Risk Factors for Obstructive Sleep apnea with Volumetric Magnetic Resonance Imaging, Am J. Respir Crit Care Med vol. 168, pp. 522-530, 2003, 9 pages.

Brian M. McGinley et al., Upper Airway Neuromuscular Compensation During Sleep is Defective in Obstructive Sleep Apnea, J Appl Physiol 105: 197-205, 2008, 10 pages.

Arie Oliven et al., Upper Airway Response to Electrical Stimulation of the Genioglossus in Obstructive Sleep Apnea, J Appl Physiol 95:2023-2029, 2003, doi:10.1152/japplphysiol.00203.2003, 8 pages.

Arie Oliven et al., Sublingual electrical stimulation of the tongue during wakefulness and sleep, Respiration Physiology 127 (2001) 217-226, 10 pages.

J.E. Remmmers et al., Pathogenesis of upper airway occlusion during sleep, 0021-8987/78/0000-0000, Copyright 1978 the American Physiological Society, 8 pages.

(56) References Cited

OTHER PUBLICATIONS

Joaquin Duran et al., Obstructive Sleep Apnea—Hypopnea and Related Clinical Features in a Population-based Sample of Subjects Aged 30 to 70 Yr, Am J Respir Crit Care Med vol. 163 pp. 685-689, 2001, 5 pages.

Anil N. Rama et al., Sites of Obstruction in Obstructive Sleep Apnea, Chest 2002; 122; 1139-1147, DOI: 10.1378/chest.122.4.1139, CHEST/122/4/Oct. 2002, 11 pages.

Astra Zeneca, Target Controlled Infusion (TCI) in Anaesthetic Practice, Convenience and Control of Intravenous Anaesthia With 'Diprivan', 5217/ Dec. 1999, 74 pages.

* cited by examiner

| SITE OF OBSTRUCTION | PATTERN OF OBSTRUCTION | | | DEGREE OF OBSTRUCTION | | |
|---|---|---|---|---|---|---|
| | A-P | LATERAL | CONCENTRIC | NONE | PARTIAL | COMPLETE |
| VELUM (SOFT PALATE) | | | N | | | N |
| ORO-PHARNYX | X | X | X | | | X |
| TONGUE-BASE | X | X | X | | | X |
| EPIGLOTTIS AND LARYNX | | | | | | |

SYSTEM AND METHOD FOR PATIENT SELECTION IN TREATING SLEEP DISORDERED BREATHING

BACKGROUND

Continuous positive airway pressure (CPAP) has been considered the primary conventional treatment for obstructive sleep apnea. However, because of the number of patients that are non-compliant or for whom the CPAP therapy is ineffective, other treatments are desirable.

Some newer therapies for treating sleep disordered breathing have been introduced. One such therapy includes the use of an implantable system for electrically stimulating the upper airway to treat obstructive sleep apnea and related dysfunction.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4 is a block diagram schematically illustrating an example physiologic determination module.

DETAILED DESCRIPTION

In the following Detailed Description, reference is made to the accompanying drawings, which form a part hereof, and in which is shown by way of illustration specific embodiments of the present disclosure that may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present disclosure. The following detailed description, therefore, is not to be taken in a limiting sense.

As used herein, the term "includes" means includes but not limited to, the term "including" means including but not limited to. The term "based on" means based at least in part on.

Embodiments of the present disclosure provide a system and method to automatically determine patient eligibility to receive an implantable upper airway stimulation system. In one example, the system and method obtains an image of, and senses physiologic data regarding, a patient's upper airway. In one aspect, this information is obtained during a formal sleep study (e.g. PSG), induced sleep, and/or induced conditions within the upper airway that mimic upper airway conditions during patient sleep. The system and method determines, based on the obtained images and sensed data, an obstruction vector that characterizes a location, a pattern, and a degree of obstruction along the upper airway. A patient candidate filter is applied against a patient health history profile. Patient eligibility for implantable upper airway stimulation is determined based on the obstruction vector and application of the patient candidate filter.

In one embodiment, one example of an implantable upper airway stimulation system (for which a patient may be determined to be eligible) is described and illustrated in association with at least WO 2010/059839, *Method of Treating Sleep Disordered Breathing*, published on May 27, 2010, and US Patent Publication 2011/0264164, *Method of Treating Sleep Disordered Breathing*, published on Oct. 27, 2011, both of which are hereby incorporated by reference in their entirety.

Figure 1:
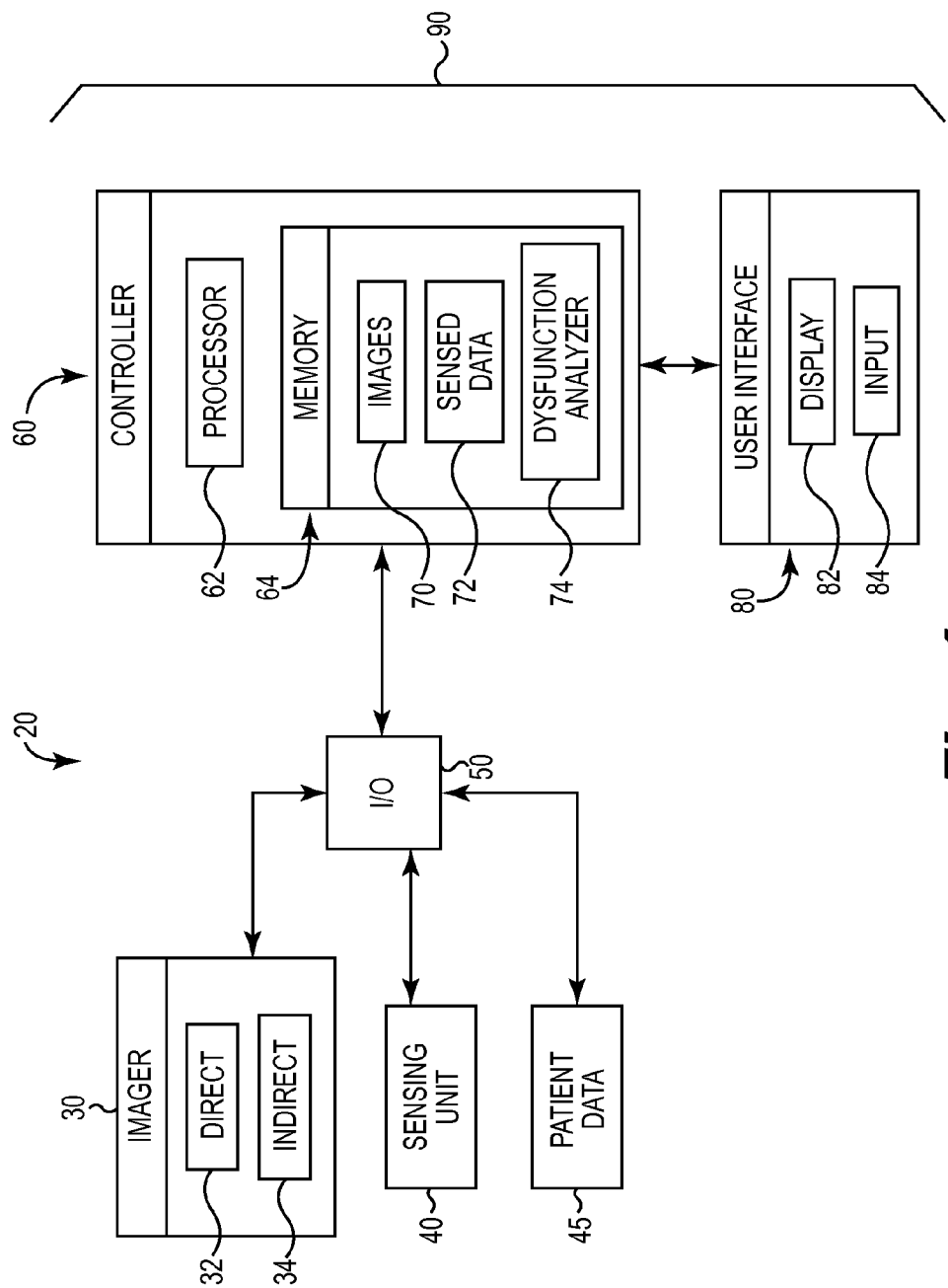
FIG. 1 is a block diagram of an example patient evaluation system.

As shown in FIG. 1, patient evaluation system 20 includes an imager 30, a sensing unit 40, a patient data resource 45, a communication input/output 50, a controller 60, and a user interface 80. In one embodiment, imager 30 captures images of an upper airway of a patient either via direct imaging module 32 or indirect imaging module 34. Direct imaging module 32 directly captures images of the structures of the upper airway, such as provided via endoscopy. Indirect imaging module 34 indirectly captures images of the structures of the upper airway via various modalities, such as ultrasound, fluoroscopy, computer axial tomography (CT), magnetic resonance imaging (MRI), and the like. Various aspects of direct and indirect imaging are further described later in association with FIG. 4.

Figure 9B:
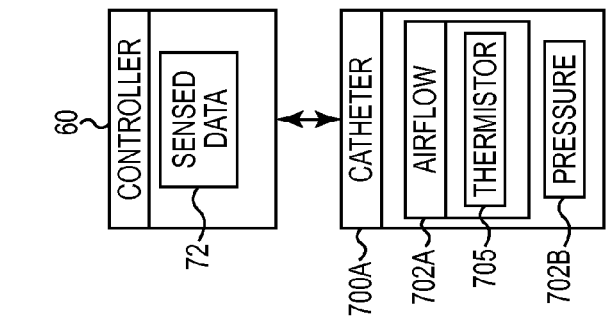
FIG. 9B is a block diagram schematically illustrating an example data sensing catheter system.

Sensing unit 40 obtains performance information about the physiologic conditions within the upper airway of a patient. Various aspects of the sensing unit 40 are further described later in association with FIG. 4, and in association with a sensing catheter (FIG. 9A) and sensing catheter system (FIG. 9B).

Figure 9A:
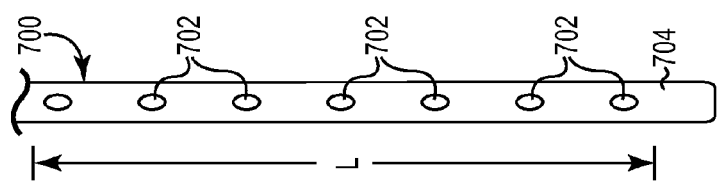
FIG. 9A is a front plan view schematically of an example data sensing catheter.

As previously noted, obstruction-related information (obtained via imager 30 and/or sensing unit 40, such as catheter 700 in FIG. 9A) is typically obtained during a formal sleep study (e.g. PSG), induced sleep, and/or induced conditions within the upper airway that mimic upper airway conditions during patient sleep.

Patient data resource 45 provides data about the general physiologic condition of a patient, such as a patient health history profile, as will be further described later in association with FIG. 2.

In one embodiment, controller 60 comprises at least one processor 62 and associated memories 64 configured to generate control signals directing the operation of system 20. In one embodiment, memory 64 stores a database of images 70, sensed data 72, and a dysfunction analyzer module 74. In response to or based upon commands received via user interface 80 and/or instructions contained in the memory 64 associated with controller 60, controller 60 generates control signals directing operation of analyzer module 74.

Images 70 include at least images taken of a patient's upper airway and sensed data 72 includes physiologic data about the patient. In one example, images 70 also includes reference images that depict known anatomical structures in the upper airway, as well as images that depict various examples of obstructions in the upper airway. In one aspect, these reference images are available for comparison to images of a particular patient candidate to automatically confirm or deny that the patient candidate has a particular location, pattern, and/or degree of obstruction within their upper airway.

In one example, the comparison of images is performed according to known objection recognition methodologies, such as a scale-invariant feature transform (SIFT) based methodology, used in computer vision applications and in image comparison applications.

In one embodiment, dysfunction analyzer module 74 uses images of a patient's upper airway and sensed data 72 about the patient's physiologic condition to analyze and determine the level of current function of a patient's upper airway. As noted above, this analysis may include the use of stored reference images for comparison with images of the upper airway of the patient candidate. In one embodiment, dysfunction analyzer module 74 includes patient candidate assessment module 150 (as described in association with FIG. 2), physiologic determination module 200 (as described in association with FIG. 4), and obstruction vector module 400 (as described in association with FIG. 5).

For purposes of this application, in reference to the controller 60 the term "processor" shall mean a presently developed or future developed processing unit that executes sequences of machine readable instructions contained in a memory. Execution of the sequences of machine readable instructions causes the processor 62 to perform actions to evaluate patient eligibility to receive an implantable upper airway stimulation system, with such actions including (but not limited to) determining an obstruction vector, applying a patient candidate filter, determining patient eligibility based on the obstruction vector and application of the patient candidate filter, etc. Memory 64 stores, among other things, images including both reference images and new images to be evaluated. In one embodiment, the instructions to be executed by processor 62 are loaded in a random access memory (RAM) for execution by the processor from a read only memory (ROM), a mass storage device, or some other persistent non-volatile storage, as represented by memory 64. In other embodiments, hard wired circuitry may be used in place of or in combination with machine readable instructions (such as software) to implement the functions described. For example, controller 60 may be embodied as part of at least one application-specific integrated circuit (ASIC). Unless otherwise specifically noted, the controller is not limited to any specific combination of hardware circuitry and/or machine readable instructions (such as software), nor limited to any particular source for the instructions executed by the processor 62.

More broadly speaking, in some embodiments, memory 64 includes, but is not limited to, volatile and nonvolatile, removable and non-removable media implemented in any method or technology for storage of information such as computer or machine readable instructions, data structures, program modules, functions, or other data. Computer storage media includes, but is not limited to, RAM, ROM, EEPROM, flash memory or other memory technology, CD, digital versatile disks (DVD) or other optical storage, magnetic cassettes, magnetic tape, magnetic disk storage or other magnetic storage devices, or any other media which can be used to store the desired information and which can be accessed by processor 62 and its related functions.

Embodiments of the present disclosure are provided in part in the general context of computer-executable instructions or machine readable instructions, such as program modules, executed by at least one computer or device. Generally, program modules include routines, programs, objects, components, data structures, etc. that perform particular tasks or implement particular data types. Typically, the functionality of the program modules may be combined and/or distributed as desired in various embodiments.

For purposes of illustration, programs, modules, functions, and/or other executable program components are illustrated as discrete blocks, although it will be understood that such programs and components reside at various times in different storage components of the computer (e.g. memory 64), and are executed by the data processor 62 of the computer.

User interface 80 is configured to enable a user to view information relating to evaluation of a patient candidate, as well as, information enabling operation and monitoring of the various functions of the patient evaluation system 20. In one aspect, user interface 80 includes a display 82 and an input device 84. In one embodiment, user interface 80 comprises a graphical user interface (GUI) that combines the display 82 and input device 84 into a single component, and which may or may not include touch pad features. In other embodiments, the display 82 and input device 84 are provided via separate or different components.

In one embodiment, patient evaluation system 20 includes a communication input/output 50, which enables communication of images and control signals between imager 30, sensing unit 40, patient data resource 45, and other components of patient evaluation system 20.

In one embodiment, controller 60, user interface 80, communication input/output 50 are combined into a computer 90.

Figure 2:
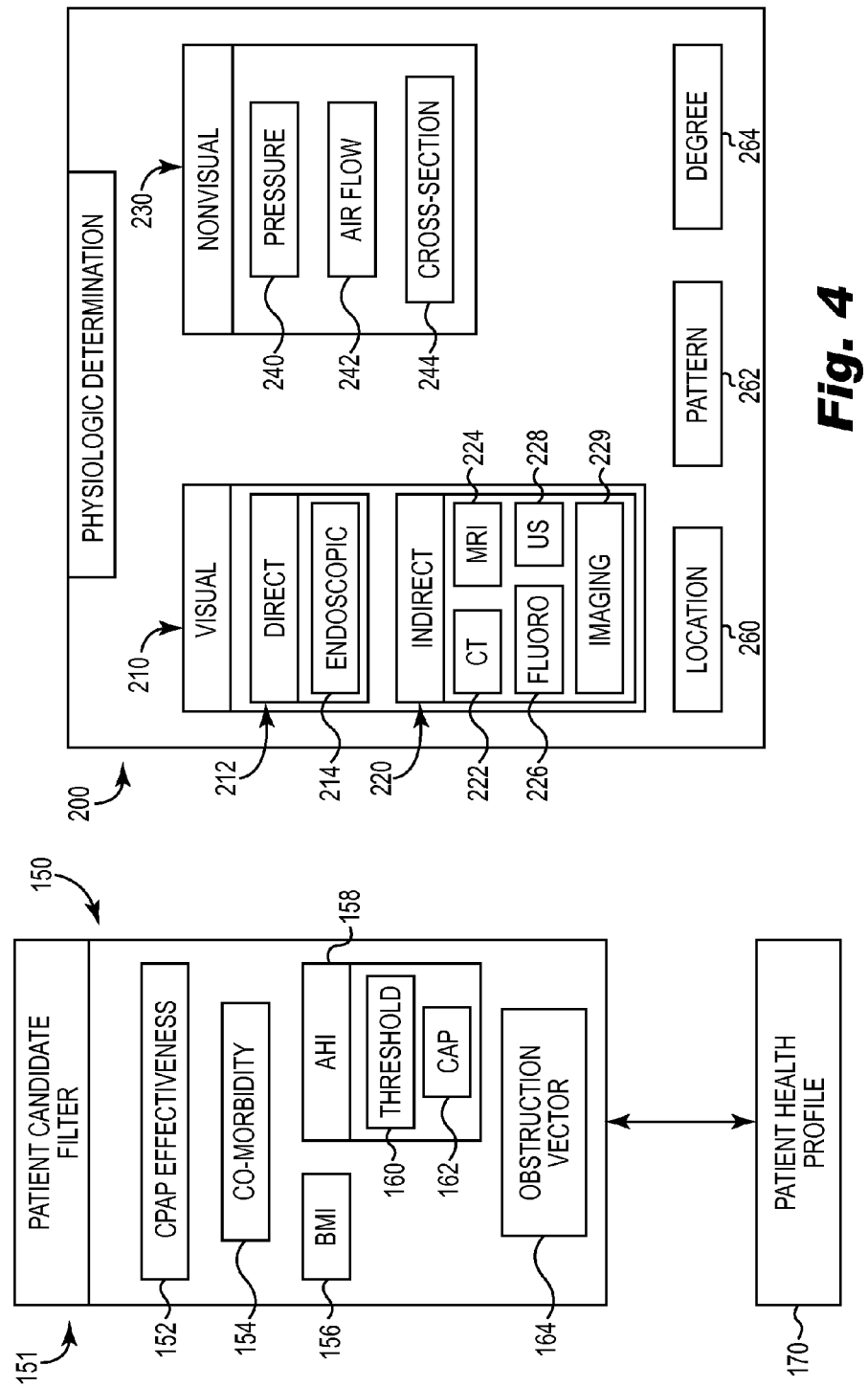
FIG. 2 is a block diagram schematically illustrating an example patient candidate filtering module.

FIG. 2 is a block diagram of a patient candidate assessment module 150, according to an embodiment of the present disclosure. As shown in FIG. 2, patient candidate assessment module 150 includes patient candidate filter 151 and patient health profile 170. In one example, patient candidate filter 151 includes CPAP effectiveness parameter 152, co-morbidity parameter 154, body-mass index (BMI) parameter 156, apnea-hypopnea index (AHI) parameter 158, and obstruction vector module 164.

Patient health profile module 170 provides a health history profile of a particular patient, with an array of data portions in which various data portions directly correspond to a respective one of the parameters of the patient candidate filter 151. With this array of data portions for a particular patient, the criteria (via parameters 152-164) of patient candidate filter 151 can be applied to the actual patient data to determine whether the particular patient is a successful candidate for treatment via implantable upper airway stimulation.

Candidates that successfully pass through filter 151 are considered target patients suitable to receive an implantable upper airway stimulation system.

Figure 3:
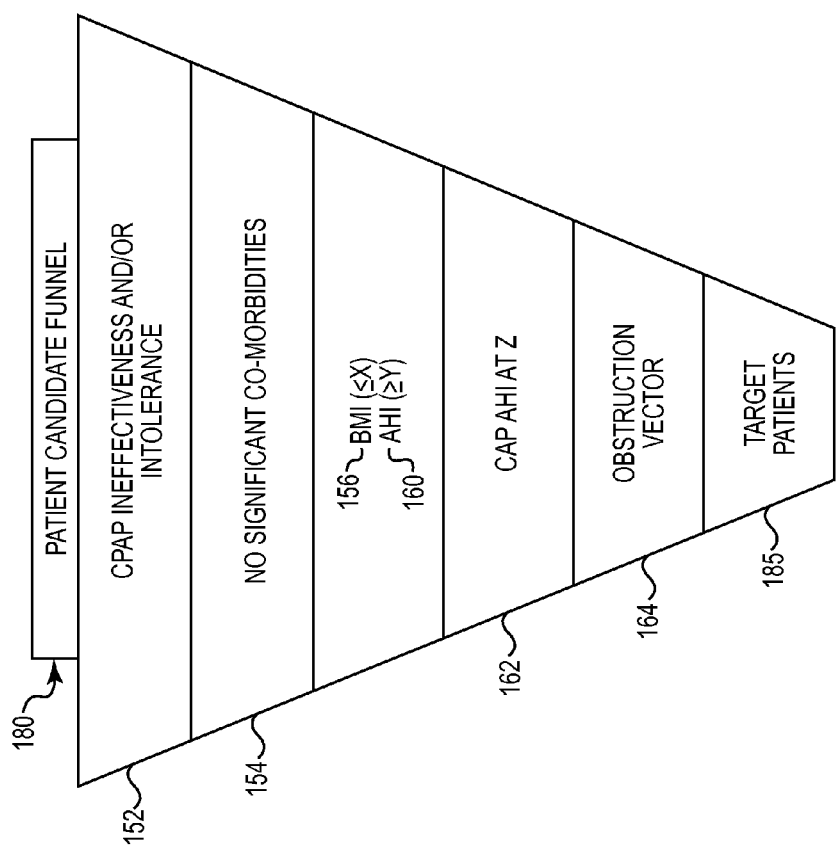
FIG. 3 is a chart schematically illustrating operation of an example patient candidate filter.

Moreover, FIG. 3 further illustrates that upon applying the parameters 152-164 of patient candidate filter 151 successively on a one-at-a-time basis, the patient candidate filter 151 (FIG. 2) acts as a funnel 180 (FIG. 3) such that a patient remains a candidate by successfully satisfying all of the parameters 152-164, and a patient is excluded by failing to achieve any one of the parameters.

It will be understood that in other embodiments, the particular order of applying the parameters of patient candidate filter 151 can be modified. Moreover, in some embodiments, additional parameters can be included as part of the patient candidate filter 151, while in other embodiments, some of the parameters 152-164 can be omitted from the patient candidate filter 151.

With reference to FIGS. 2-3, CPAP parameter 152 establishes criteria for inclusion as a patient candidate when CPAP therapy is ineffective for a particular patient and/or when the patient is intolerant of CPAP therapy. Co-morbidity parameter 154, as shown in FIGS. 2-3, establishes criteria for inclusion as a patient candidate when the patient lacks significant co-morbidities. In one example, the significant co-morbidities for which a patient would be excluded include at least chronic obstructive pulmonary disease (COPD), drug-resistant hypertension, neuromuscular diseases, and renal failure. In other words, via co-morbidity parameter 154, a patient having at least one of these co-morbidities would be excluded from being a candidate for receiving implantable upper airway stimulation. In some embodiments, via co-morbidity parameter 154, congestive heart failure and stroke are also criteria for excluding a patient from eligibility when those co-morbidities are relatively severe. In one aspect, via co-morbidity parameter 154, a score is assigned to the relative severity level of the co-morbidities to distinguish their relative severity and a threshold of severity is established for which a patient would be excluded.

However, it will be understood that not all co-morbidities would prevent a patient from being a candidate for implantable upper airway stimulation because certain co-morbidities actually improve upon successful treatment of sleep disordered breathing. For example, the patient conditions of hypertension (other than drug-resistant hypertension), congestive heart failure, and stroke often improve upon treatment of sleep disordered breathing (such as obstructive sleep apnea) via an implantable upper airway stimulation system. In one aspect, using the previously described severity threshold and a score assigned to represent the relative severity of the patient's own co-morbidities (stored in the patient health history profile), the patient candidate filter 151 can distinguish whether the hypertension, congestive heart failure, and/or stroke are moderate enough to retain the patient as being patient eligible.

Body-mass index (BMI) parameter 156 is shown in FIGS. 2-3 and establishes criteria for inclusion as a patient candidate via a cap (X) for the body-mass index of the patient. A patient with a BMI below that cap (X) would be included as a patient candidate while a patient with a BMI above that cap (X) would be excluded. In one example, the BMI cap is set at 32, while in other examples, the BMI cap can be set higher or lower than 32.

With further reference to FIGS. 2-3, AHI threshold parameter 158 establishes criteria for inclusion as a patient candidate having an apnea-hypopnea index (AHI) equal to or greater than a quantity (Y). In one example, the threshold parameter Y is 20.

Accordingly, in one example, a patient with a BMI higher than 32 and/or with an AHI less than 20 would be excluded from the patient eligible group while patients with a BMI of 32 or lower and having an AHI above 20 would be included in a patient eligible group. In other embodiments, the parameter X of the BMI index is set at less or more than 32 while the parameter Y of the AHI index is set at less or more than 20.

The AHI cap parameter 162 establishes criteria for inclusion of a patient candidate upon their AHI index not exceeding a maximum AHI index. In other words, the AHI cap parameter 162 sets a cap (Z). Accordingly, a patient exhibiting AHI higher than the cap (Z) would be excluded from the patient eligible group. In one non-limiting example, AHI cap (Z) 162 is set at 50. In other embodiments, the cap (Z) is set at less or more than 50.

It will be understood that in some embodiments, the parameters are applied in a different order, and that in some embodiments, more or less criteria can be applied than the parameters shown in diagram 180 of FIG. 3.

With further reference to FIGS. 2-3, obstruction vector module 164 establishes criteria for inclusion of a patient candidate based on an obstruction vector parameter relating to a location, pattern, and degree of obstruction. In one aspect, obstructions at particular locations (e.g. tongue-base), obstructions having particular patterns (e.g. antero-posterior), or obstructions having particular degrees (e.g. partial or complete) are established as criteria for including a patient candidate. In another example, a combination of obstruction related data are combined into a single vector quantitatively representing the combined effect of the location, pattern, and degree of obstruction.

Such obstruction vectors can be used to establish a criteria for inclusion (e.g., tongue-base location, antero-posterior pattern, and complete degree) or for exclusion as further described below. In one example, an obstruction located at the soft palate region, having a circular pattern, and being complete (at least 75% constriction) is expressed as a single vector and established as criteria to exclude a patient. Accordingly, upon such information being part of a patient's health history profile and/or obtained via imaging and sensed data, application of the patient candidate filter 151 would lead to excluding the patient from eligibility for receiving an implantable upper airway stimulation system.

As shown in FIG. 3, target patients parameter 185 denotes patients that remain eligible after screening via parameters 152-164.

FIG. 4 schematically illustrates a block diagram of a physiologic determination module 200, according to an embodiment of the present disclosure. As shown in FIG. 4, physiologic determination module 200 includes a visual imaging module 210 and a non-visual sensing module 230, as well as type parameter 260, location parameter 262, and degree parameter 264.

In one embodiment, the visual imaging module 210 includes a direct imaging module 212 and an indirect imaging module 220. The direct imaging module 212 includes an endoscopic imaging function 214 and obtains direct images of the upper airway of the patient via endoscopy. In general terms, the indirect imaging module 220 obtains indirect images of the upper airway of the patient. In one embodiment, the indirect imaging module 220 includes computer axial tomography (CT) function 222, magnetic resonance imaging (MRI) function 224, a fluoroscopy function 226, an ultrasound (US) function 228, and an other imaging function 229. In one aspect, CT function 222 provides information about the upper airway based on images of the upper airway captured via computer tomography, while MRI function 224 provides information about the upper airway based on images of the upper way captured via magnetic resonance imaging 224. Fluoroscopy function 226 provides information about the upper airway based on images of the upper airway captured via fluoroscopy while ultrasound function 228 provides information about the upper airway based on images of the upper airway captured via ultrasound. Other imaging function 229 provides image of the upper airway through alternate imaging mechanisms.

Figures 5, 6:
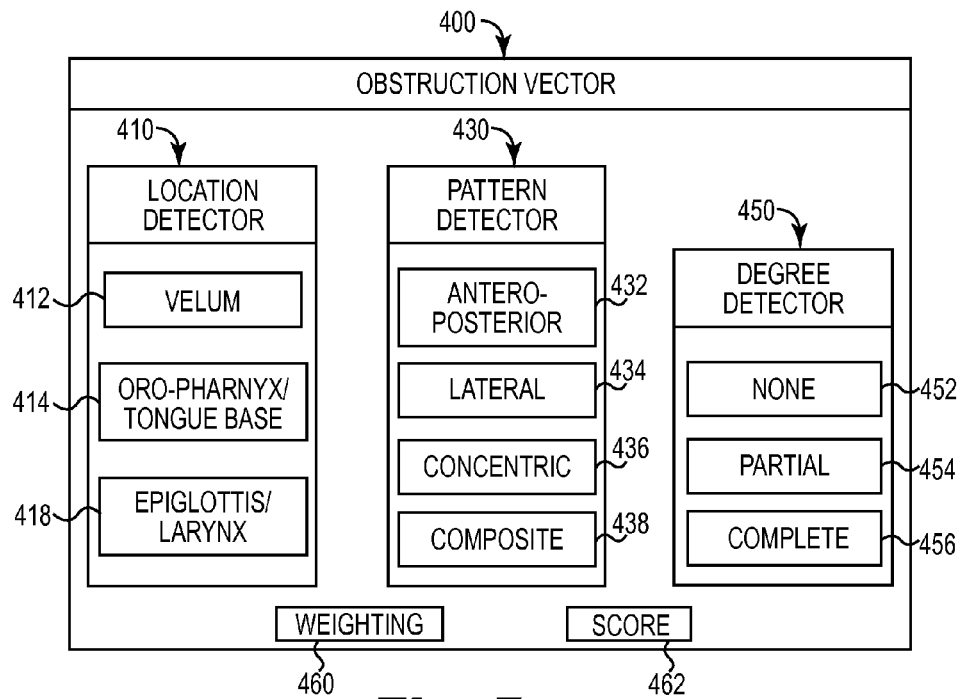
FIG. 5 is a block diagram schematically illustrating an example obstruction vector module.
FIG. 6 is a chart schematically illustrating an example obstruction information grid.

The non-visual sensing module 230 includes a pressure function 240, an airflow function 242, and a cross-section area function 244. The pressure function 240 provides information about air pressure measured directly within the upper airway portion of a patient, while air flow function 242 provides information about an air flow measured within an upper airway of a patient. The measured air flow can pertain to a velocity of air flow and/or a volume of air flow. In each case, the respective pressure and/or airflow are measured at varying levels or locations along the upper airway of the patient in cooperation with the site detector module 410 (FIG. 5). In one embodiment, the area function 244 provides information about the cross-sectional area of the upper airway of the patient at varying locations along the upper airway, in cooperation with location detector module 410 (FIG. 5), sensing catheter 700 (FIG. 9A), and sensing catheter system 750 (FIG. 9B). The area function 244 obtains such information via at least direct imaging via direct imaging module 212 and/or indirect imaging module 220.

The images obtained via visual module 210 and the data sensed via non-visual module 230 of physiologic determination module 200 supply an array of physiologic information about the upper airway of a patient. In one embodiment, at least some of this information about the upper airway portion of a patient is categorized according to a location parameter 260, a pattern parameter 262, and/or a degree parameter 264. In one aspect, the location parameter 260 denotes a location or site at which an obstruction takes place, such as which portion along the upper airway is located vertically and in relation to which anatomical structures. The various sites or locations of obstruction are further described later in association with FIGS. 5-6 and 9. In another aspect, the pattern parameter 262 denotes a type or pattern of obstruction, such as whether the obstruction forms laterally, concentrically, etc. The various types or patterns of obstruction are further described later in association with FIGS. 5-7C. In another aspect, the degree parameter 264 denotes the extent to which the upper airway is obstructed. The various degrees of obstruction are further described later in association with FIGS. 5-7C.

FIG. 5 is a block diagram schematically illustrates an obstruction vector module 400, according to an embodiment of the present disclosure. As shown in FIG. 5, obstruction evaluation module 400 includes location detector module 410, pattern detector module 430, and degree detector module 450.

In general terms, the location detector module 410 operates to identify a site along the upper airway at which an obstruction occurs and which is believed to cause sleep disordered breathing. In one embodiment, the location detector module 410 includes a velum (soft palate) parameter 412, an oropharnyx-tongue base parameter 414, and an epiglottis/larynx parameter 418. Each respective parameter denotes an obstruction identified in the respective physiologic territories of the velum (soft palate), oropharnyx-tongue base, and epiglottis which are generally illustrated for an example patient in FIG. 8. In one aspect, these distinct physiologic territories define an array of vertical strata within the upper airway. Moreover, each separate physiologic territory (e.g. vertical portion along the upper airway) exhibits a distinct characteristic behavior regarding obstructions and associated impact on breathing during sleep. Accordingly, each physiologic territory responds differently to implantable upper airway stimulation.

Figure 8:
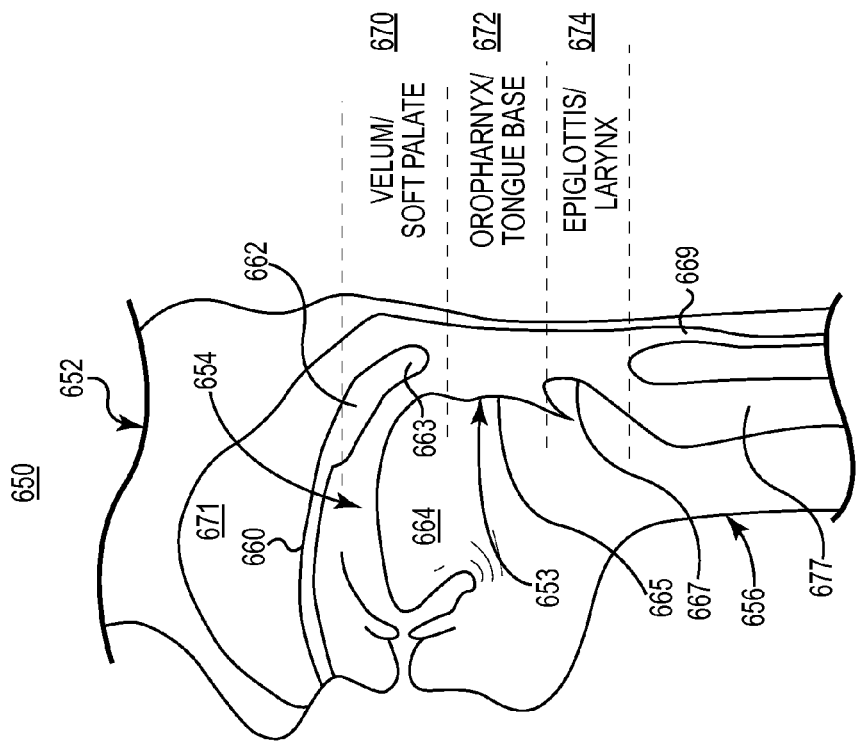
FIG. 8 is a side view schematically illustrating one example of a patient's upper airway.

With this in mind, the velum (soft palate parameter 412 denotes obstructions taking place in the level of the region of the velum (soft palate), as illustrated in association with FIG. 8. As shown in FIG. 8, a diagram 650 provides a side sectional view (cross hatching omitted for illustrative clarity) of a head and neck region 652 of a patient. In particular, an upper airway portion 653 extends from the mouth region 654 to a neck portion 656. The upper airway portion 653 includes a velum (soft palate) region 670, an oropharnyx-tongue base region 672, and an epiglottis region 674. The velum (soft palate) region 670 includes an area extending below sinus 671, and including the soft palate 670, approximately to the point at which tip 663 of the soft palate 662 meets a portion of tongue 664 at the back of the mouth 654. The oropharnyx-tongue base region 672 extends approximately from the tip of the soft palate 662 (when in a closed position) along the base 665 of the tongue 664 until reaching approximately the tip region of the epiglottis 667. The epiglottis-larynx region 672 extends approximately from the tip of the epiglottis 667 downwardly to a point above the esophagus 669.

As will be understood from FIG. 8, each of these respective regions 670, 672, 674 within upper airway portion 654 correspond the respective velum parameter 412, oropharnyx-tongue base parameter 414, and epiglottis parameter 416, respectively of FIG. 5.

With further reference to FIG. 5, in general terms the pattern detector module 430 enables detecting and determining a particular pattern of an obstruction of the upper airway portion 654, and in one embodiment, operates in cooperation with physiologic determination module 200 (as previously described in FIG. 3) to do so. In one embodiment, the pattern detector module 430 includes an antero-posterior parameter 432, a lateral parameter 434, a concentric parameter 436, and composite parameter 438.

Figure 7A:
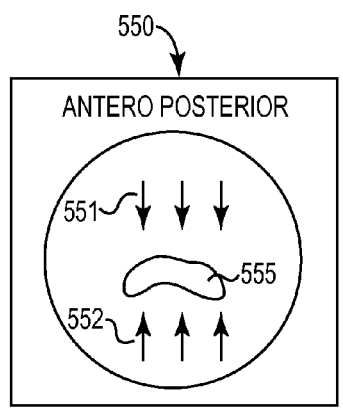
FIGS. 7A-7C is a series of diagrams depicting examples of various types, degrees, and locations of obstructions of an upper airway.

The antero-posterior parameter 432 of pattern detector module 430 (FIG. 5) denotes a collapse of the upper airway that occurs in the antero-posterior orientation, as further illustrated in the diagram 550 of FIG. 7A. In FIG. 7A, arrows 551 and 552 indicate one example direction in which the tissue of the upper airway collapses, resulting in the narrowed air passage 555. FIG. 7A is also illustrative of a collapse of the upper airway in the soft palate region 670, whether or not the collapse occurs in an antero-posterior orientation. For example, in some instances, the velum (soft palate) region exhibits a circular pattern of collapse, as shown in diagram 570 of FIG. 7B.

Figure 7B:
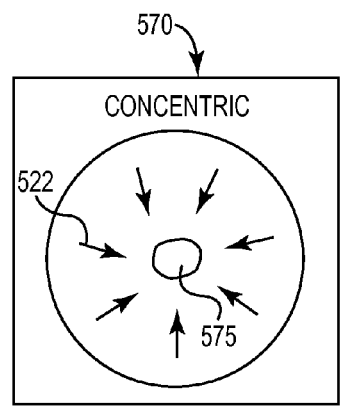

The concentric parameter 436 of pattern detector module 430 (FIG. 5) denotes a collapse of the upper airway that occurs in a concentric orientation, as further illustrated in the diagram 570 of FIG. 7B. In FIG. 7B, arrows 572 indicate the direction in which the tissue of the upper airway collapses, resulting in the narrowed air passage 575.

Figure 7C:
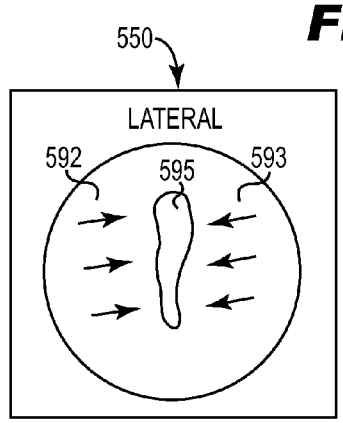

The lateral parameter 434 of pattern detector module 430 (FIG. 5) denotes a collapse of the upper airway that occurs in a lateral orientation, as further illustrated in the diagram 590 of FIG. 7C. In FIG. 7C, arrows 592 and 593 indicate the direction in which the tissue of the upper airway collapses, resulting in the narrowed air passage 595.

The composite parameter 438 of pattern detector module 430 (FIG. 5) denotes a collapse of the upper airway portion 653 that occurs via a combination of the other mechanisms (lateral, concentric, antero-posterior) or that is otherwise ill-defined from a geometric viewpoint but that results in a functional obstruction of the upper airway portion 653.

With further reference to obstruction vector module of FIG. 5, in general terms the degree detector module 450 indicates a relative degree of collapse or obstruction of the upper airway portion 653. In one embodiment, degree detector module 450 includes a none parameter 452, a partial parameter 454, and a complete parameter 456. The none parameter 452 corresponds to a collapse of 25 percent or less, while the partial collapse parameter 454 corresponds to a collapse of between about 25 to 75%, and the complete collapse parameter 456 corresponds to a collapse of greater than 75 percent.

It will be understood that various patterns of collapse occur at different levels of the upper airway portion and that the level of the upper airway in which a particular pattern of collapse appears can vary from patient-to-patient.

In some embodiments, obstruction vector module 400 comprises a weighting function 460 and score function 462. In general terms, the weighting function 460 assigns a weight to each of the location, pattern, and/or degree parameters (FIGS. 4 and 5) as one or more those respective parameters can contribute more heavily to the patient exhibiting sleep disordered breathing or to being more responsive to implantable upper airway stimulation. More particularly, each respective parameter (e.g. antero-posterior 432, lateral 434, concentric 436, composite 438) of each respective detector modules (e.g. pattern detector module 430) is assigned a weight corresponding to whether or not the patient is eligible for receiving implantable upper airway stimulation. Accordingly, the presence of or lack of a particular pattern of obstruction (or location or degree) will be become part of an overall score (according to score parameter 462) for an obstruction vector indicative how likely the patient will respond to therapy via an implantable upper airway stimulation system.

FIG. 6 is a chart 500 that combines information from the location parameter 260, the pattern parameter 262, and degree parameter 264 into a single informational grid or tool by which the obstruction is documented for a particular patient. By using the combination of parameters, the informational tool is programmed to automatically indicate whether or not a particular patient is a good candidate to receive implantable upper airway stimulation. As shown in FIG. 6, in one example a patient having an obstruction at the oropharnyx-tongue base, with a complete obstruction or partial obstruction, with any of the patterns of obstruction, would be a good candidate. On the other hand, a patient having a concentric pattern of obstruction that is complete at the velum (soft palate) would be a poor candidate, and not receive an implantable upper airway stimulation system. This decision logic stems from fact that an implantable upper airway stimulation system activates a nerve (such as the hypoglossal nerve), which causes protrusion of tongue to restore airway patency in the oropharnyx-tongue base region whereas such stimulation generally does not alleviate obstructions as the soft palate region.

FIG. 9A is a plan view of catheter 700, according to an embodiment of the present disclosure. As shown in FIG. 9, a flexible sensing catheter 700 is configured to be placed longitudinally in the airway during sleep to determine via sensors 702 the greatest site(s) of obstruction or narrowing vertically along the airway. In some embodiments, sensors 102 sense pressure, air flow, and/or cross sectional area. Because distal portion 704 of catheter 700 has a known length (L) along the array of sensors 702, this information can help locate a vertical position of a site of narrowing or obstruction in the upper airway. Accordingly, in combination with visual observation via endoscopy (which helps identify a type and/or degree of obstruction relative to generally horizontal cross-section of the upper airway), the pressure measurement and/or air flow measurement yields information regarding the location, pattern, and degree of obstruction.

In one embodiment, sensors 702 include one or more thermistors provided for sensing airflow. In one aspect, this airflow sensing is performed in a manner consistent as described in Akre et al, *Advantages of Measuring Air Flow in the Pharynx with Internal Thermistors*, European Archives of Oto-Rhino-Laryngology, Vol. 257, Number 5, 251-255 (2007).

In one embodiment, sensors 702 include one or more pressure sensors provided for substantially simultaneously sensing pressure at different locations along the upper airway to locate the site of an obstruction. In one aspect, this pressure airflow sensing is performed in a manner consistent as described in Tvinnereim et al, *Pressure Recordings A Method For Detecting Site of Upper Airway Obstruction In Obstructive Sleep Apnea*, Acta Otolaryngol (Stockh) 1992; Suppl, 492:132-40, Woodson et al, *A Multisensor Solid-State Pressure Manometer To Identify The Level of Collapse In Obstructive Sleep Apnea*, Otolaryngol Head Neck Surg 1992; 107: 651-6, and Skatvedt, *Continuous Pressure Measurements In The Pharnyx and Esophagus During Sleep In Patients With Obstructive Sleep Apnea Syndrome*, Laryngoscope 1992; 102:1275-80.

In some embodiments, a single catheter carries both thermistors and pressure sensors located throughout a length of distal portion of catheter 700.

It is to be understood that the features of the various exemplary embodiments described herein may be combined with each other, unless specifically noted otherwise.

As shown in FIG. 9B, sensing catheter system 750 operates as part of or in cooperation with patient evaluation system 20 (FIG. 1) and in one example, includes at least catheter 700A and controller 60 (FIG. 1). The catheter 700A includes an airflow sensor 702A and a pressure sensor 702B. In one embodiment, the airflow sensor 702A is a thermistor 705, as previously described above.

The data sensed via catheter 700A is communicated to controller 60 and stored as sensed data 72, and used for evaluating patient eligibility in the manner previously described in association with FIGS. 1-9A.

Embodiments of the present disclosure provide a consistent, reliable way of automatically assessing patient eligibility for receiving an implantable upper airway system, which in turn increases the likelihood of efficacy of such systems.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for screening patients comprising:
at least one of:
obtaining an image, via an imaging device, of a portion of an upper airway of a patient; and
sensing data, via a catheter insertable into the upper airway, regarding a portion of an upper airway of a patient, wherein the sensed data comprises at least one of a pressure and an airflow during respiration; and automatically, via execution in a computer processor of machine readable instructions stored in non-volatile memory, performing:
determining, based on the obtained image and sensed data, an obstruction vector including a location, a pattern, and a degree of obstruction along the upper airway;
applying a patient candidate filter against a patient health profile; and
determining patient eligibility for implantable upper airway stimulation based on the obstruction vector and application of the patient candidate filter.

2. The method of claim 1, wherein applying the patient candidate filter comprises:
applying an array of parameters, one parameter at a time in succession, where a failure of the patient health history profile to match a respective one of the parameters of the patient candidate filter results in denial of patient eligibility.

3. The method of claim 2, wherein applying the series of parameters includes:
applying at least one of a continuous positive airway pressure (CPAP) parameter, a co-morbidity parameter, a body mass index (BMI) maximum parameter, an apnea-hypopnea index (AHI) threshold parameter, and an apnea-hypopnea index (AHI) cap parameter.

4. The method of claim 1, wherein determining the obstruction vector comprises characterizing the location of obstruction as least one of a velum location, an oropharnyx-tongue base location, and an epiglottis-larynx location.

5. The method of claim 4, wherein determining the obstruction vector comprises:
characterizing the pattern of obstruction as at least one of an antero-posterior pattern, a lateral pattern, a concentric pattern, and a composite pattern.

6. The method of claim 5, wherein determining the obstruction vector comprises:
characterizing the degree of obstruction as at least one of a non-existent obstruction, a partial obstruction, and a complete obstruction.

7. The method of claim 1, wherein determining the obstruction vector includes:
calculating and assigning a score representing the location, pattern, and degree of obstruction.

8. The method of claim 7, wherein determining the obstruction vector includes:
applying a weighting factor to at least one of the location, pattern, and degree of the obstruction.

9. The method of claim 1, wherein the imaging device comprises at least one of:
a direct imaging device to obtain a direct image of the portion of the upper airway including at least endoscopic imaging; and
an indirect imaging device to obtain an indirect image of the portion of the upper airway.

10. The method of claim 9, wherein the indirect imaging device comprises:
at least one of a computer tomography function, a magnetic resonance imaging function, a fluoroscopy function, and an ultrasound function.

11. The method of claim 1, wherein sensing data via the catheter comprises:
arranging the catheter with a distal portion including at least an array of pressure sensors and an array of airflow sensors, wherein the sensors of each respective array are spaced apart from each other longitudinally along a length of the distal portion of the catheter.

12. A system for patient selection for treatment of sleep disordered breathing, the system comprising:
an imager to obtain images of an upper airway of a patient; and
a patient evaluation module including a computer processor to execute machine readable instructions, stored in a non-volatile memory, to determine patient eligibility via:
a physiologic determination module cooperative with the imager to determine a location, pattern, and a degree of obstruction within the upper airway based on the images;
a patient candidate filter to apply an array of patient candidate parameters against a patient health profile to produce patient candidate information; and
an obstruction vector module to determine an obstruction vector based on the determined location, pattern, and degree of obstruction, wherein the patient evaluation module uses the patient candidate information and the obstruction vector to automatically determine patient eligibility for implantable upper airway stimulation.

13. The system of claim 12, comprising
an elongate flexible sensing catheter including at least one of an array of pressure sensors and an array of airflow sensors, each array extending longitudinally along a distal portion of the catheter, wherein the sensing catheter is in communication with a controller to provide sensed data to the patient evaluation module.

14. The system of claim 13, wherein both the obstruction vector module uses the sensed data in combination with the images to determine the obstruction vector regarding the location, pattern, and degree of obstruction.

15. The system of claim 14, wherein the obstruction vector is configured to calculate and assign a score representing the location, pattern, and degree of obstruction.

16. The system of claim 14, wherein the obstruction vector is configured to apply a weighting factor to at least one of the location, pattern, and degree of the obstruction.

17. The system of claim 14 wherein the obstruction vector module includes a location parameter to characterize, based on at least one of the images and the sensed data, the location of obstruction as least one of a velum location, an oropharnyx-tongue base location, and an epiglottis-larynx location.

18. The system of claim 17, wherein the obstruction vector comprises:
a pattern detector module configured to characterize, based on at least one of the images and sensed data, the pattern of obstruction as at least one of an antero-posterior pattern, a lateral pattern, a concentric pattern, and a composite pattern.

19. The system of claim 18, wherein the obstruction vector comprises:
a degree detector module configured to characterize, based on at
least one of the images and sensed data, the degree of obstruction as at least one of a non-existent obstruction, a partial obstruction, and a complete obstruction.

20. The system of claim 12, wherein the patient candidate filter is configured to apply an array of parameters, one parameter at a time in succession, where a failure of the patient health history profile to match a respective one of the parameters of the patient candidate filter results in denial of patient eligibility.

21. The system of claim 18, wherein the array of parameters includes a continuous positive airway pressure (CPAP) parameter, a co-morbidity parameter, a body mass index (BMI) maximum parameter, an apnea-hypopnea index (AHI) threshold parameter, and an apnea-hypopnea index (AHI) cap parameter.

* * * * *